United States Patent
Procino et al.

(10) Patent No.: US 10,139,368 B2
(45) Date of Patent: Nov. 27, 2018

(54) PROCESS AND SYSTEM FOR FACILITATING CHEMICAL IDENTIFICATION IN A DETECTOR

(71) Applicant: Smiths Detection-Watford Limited, Hemel Hempstead (GB)

(72) Inventors: Immacolata Procino, Hemel Hempstead (GB); Paul Douglas Arnold, Hemel Hempstead (GB)

(73) Assignee: SMITHS DETECTION-WATFORD LIMITED, Hertfordshire (GB)

( * ) Notice: Subject to any disclaimer, the term of this patent is extended or adjusted under 35 U.S.C. 154(b) by 0 days.

(21) Appl. No.: 15/529,182

(22) PCT Filed: Nov. 24, 2015

(86) PCT No.: PCT/GB2015/053581
§ 371 (c)(1),
(2) Date: May 24, 2017

(87) PCT Pub. No.: WO2016/083795
PCT Pub. Date: Jun. 2, 2016

(65) Prior Publication Data
US 2017/0356878 A1 Dec. 14, 2017

(30) Foreign Application Priority Data
Nov. 25, 2014 (GB) .................................. 1420939.9

(51) Int. Cl.
*G01N 27/62* (2006.01)
*G01N 33/00* (2006.01)

(52) U.S. Cl.
CPC ....... *G01N 27/622* (2013.01); *G01N 33/0057* (2013.01)

(58) Field of Classification Search
CPC .................. G01N 27/622; G01N 33/0057
See application file for complete search history.

(56) References Cited

U.S. PATENT DOCUMENTS 5,450,193 A * 9/1995 Carlsen .................. A61B 5/083 356/246
2006/0078502 A1* 4/2006 Dewanjee ............ A61K 49/101 424/9.361

(Continued)

FOREIGN PATENT DOCUMENTS

WO 2015173579 A1 11/2015

OTHER PUBLICATIONS

Daum, Keith A. et al., "Formation of halide reactant ions and effects of excess reagent chemical on the ionization of TNT in ion mobility spectrometry", Talanta 55 (2001), 491-500.

(Continued)

*Primary Examiner* — Nicole Ippolito
*Assistant Examiner* — Sean Luck
(74) *Attorney, Agent, or Firm* — Kevin E. West; Advent, LLP (57) ABSTRACT

The present disclosure relates to a process for facilitating the identification of target chemicals which may be detected by means of an ion mobility spectrometer and a system for implementing the same. In an aspect of the disclosure, there is provided a process for determining the ratio of $Cl^-$ to $Cl^-.OOH$ reactant ion species formed in a pentachloroethane doped ion mobility spectrometer operating in negative mode, said process comprising: i) introducing a sample comprising or consisting essentially of isoflurane into a pentachloroethane doped ion mobility spectrometer; ii) collecting data relevant to the detection of two isoflurane monomer ions formed following reaction with $Cl^-$ and $Cl^-.OOH$ reactant ion species present in the pentachloroethane doped ion mobility spectrometer; and iii) determining the ratio of $Cl^-$ to $Cl^-.OOH$ reactant ion species formed in the pentachloroethane doped ion mobility spectrometer based on an evaluation of the data collected.

19 Claims, 2 Drawing Sheets

Process flow chart

101 Ionisation of a sample comprising or consisting essentially of isoflurane through reaction with Cl⁻ and Cl⁻OOH reactant ions formed in the PCE doped IMS.

102 Detection of negative isoflurane monomer ions formed following ionisation.

103 Collection of data relevant to the detection of isoflurane monomer ions.

104 Determination of ratio of Cl⁻ and Cl⁻OOH reactant ions in the PCE doped IMS based on an evaluation of the data.

(56) References Cited

U.S. PATENT DOCUMENTS

2012/0288537 A1* 11/2012 Schwendeman ............................ A61K 47/48015
                                                                                                                               424/400
2016/0272940 A1*  9/2016 Chung ................... A61K 35/30

OTHER PUBLICATIONS

Eiceman, G. A. et al., "Ion Mobility Spectrometry of Halothane, Enflurane, and Isoflurane Anesthetics in Air and Respired Gases", Anal. Chem, 1989, 61, 1093-1099.
Gunzer, Frank et al., "Investigation of ion cluster formation in a pulsed ion mobility spectrometer operating in the negative mode", Sensors and Actuators B 204 (2014) 467-473.
Karpas, Zeev et al., "Qualitative and quantitative response characteristics of a capillary gas chromatograph/ion mobility spectrometer to halogenated compounds", Analytica Chimica Acta, 282 (1993) 19-31.
Lawrence, A. H. et al., "Detection of Ethylene Glycol Dinitrate Vapors by Ion Mobility Spectrometry Using Chloride Reagent Ions", Anal. Chem. 1988, 60, 104-109.
GB Search Report dated May 27, 2017 for GB Application No. GB1420939.9.
International Search Report dated Feb. 16, 2016 for Application No. PCT/GB2015/053581.

* cited by examiner

Figure 1: Process flow chart

Figure 2:

Figure 3: PCE related RIPs obtained for different concentrations of PCE in the reaction region of the IMS detector are shown in the top IMS spectra. The respective IMS isoflurane response is shown in the bottom spectra.

Figure 4: PCE related RIP obtained in a "wet" IMS system is shown in the top IMS spectrum where the identity of the ion species underneath the RIP is unknown (?). The respective IMS isoflurane response is shown in the bottom spectrum, where two monomer ion peaks are identifiable.

PROCESS AND SYSTEM FOR FACILITATING CHEMICAL IDENTIFICATION IN A DETECTOR

The present disclosure relates to a process for facilitating the identification of target chemicals which may be detected by means of an ion mobility spectrometer. More particularly, the disclosure relates to a process comprising the use of isoflurane for facilitating the identification of target chemicals in a sample analysed using a pentachloroethane doped negative mode ion mobility spectrometer.

Ion mobility spectrometry (IMS) is an analytical technique that is capable of separating gas-phase ions according to their size to charge ratios as a result of interaction of the ions with a buffer gas in an electric field. IMS is capable of identifying chemicals based on the time taken for the ionised chemical to traverse a drift chamber separating an ioniser and a detector. The output of an IMS detector can be visually represented graphically as a "mobility spectrum" of peak height versus the ion's time of flight ("drift time").

The velocity of travel of ions in a buffer gas in the drift chamber under the influence of an electric field is typically affected by field strength, nature of the buffer gas, temperature and pressure, in addition to the physical characteristics of the ion. A qualitative measure of a particular ion in the context of IMS is the ion mobility constant (K), which derives from the ion's velocity and the electric field strength. Commonly, the ion mobility constant is modified and reported as a reduced mobility constant ($K_0$), which corresponds to a measured mobility constant corrected to standard pressure and temperature. Reduced mobility values, amongst other spectral data obtainable from IMS, can be used for chemical identification purposes.

Ion mobility spectrometers have been utilised in numerous applications, most notably in the detection of chemical warfare agents, explosives and illicit drugs, due to their high sensitivity, portability, facile operation and fast response time, which have made them invaluable devices for military, police and security personnel. Ion mobility spectrometers have also been used in the detection of biological materials, including as part of medical diagnostic devices, as well as for the continuous monitoring of airborne molecular contamination.

Dopants may be used in conjunction with IMS for improving sensitivity and/or selectivity of the IMS detector for the detection of target chemicals. In particular, dopants are known to influence the ion-molecule chemistry in the sample ionisation region of IMS detectors, affecting the composition of ions produced in the reaction region, and to modify conditions affecting the drift of ions. An effective dopant is generally considered to be a compound with sufficient electron affinity to lead to preferential ionization of target chemicals for detection, whilst blocking potential interferences.

Typically, a dopant is ionized to first form ions of relatively stable composition whilst preventing other species in the carrier gas with lower electron affinity from participating in the ionization reaction, thereby reducing interference. Meanwhile, as the electron affinity of the target chemicals is higher than the dopant molecules, the ions formed interact with chemicals of a sample to generate molecular ions for subsequent detection. Addition of a dopant may also enable the spectrum peak position of product ions to shift. This can be an advantage when, in the absence of a particular dopant, a product ion peak is located in a spectral region of overlapping peaks, whereas the presence of the dopant separates the product ion peak to facilitate identification.

IMS may be operated, although not simultaneously, either in a negative mode or a positive mode, depending on whether a negative or positive electric field gradient is applied respectively. Historically, detection of analytes forming positive ions in an ion mobility spectrometer, and thus detected in the positive mode, has predominantly related to the detection of narcotics whilst the detection of explosives more often occurs in the negative mode. Nevertheless, IMS detectors operating in the negative mode have wide utility and have also been used for the detection of industrial chemicals and chemical warfare agents. Common dopants for positive mode IMS include acetone and ammonia, whilst common dopants for negative mode IMS include chloride and halogenated hydrocarbons, such as hexachloroethane (HCE; CAS #67-72-1) and pentachloroethane (PCE; CAS #76-01-1).

IMS detectors may be heated such that the temperature inside the detector is controlled. Alternatively, IMS detectors may be unheated such that temperature varies depending on the prevailing environmental factors. Generally, in heated IMS detectors where temperature is typically higher, the presence of moisture in the carrier gas has an insignificant effect on the dominant chemistry within the reaction region of the detector. This contrasts with unheated IMS detectors, where moisture in the carrier gas can have a significant effect on the dominant chemistry within the reaction region of the detector. For example, the level of moisture can determine the type and proportion of reactant ions which are formed following ionisation. Thus, although unheated IMS detectors offer a greater portability and can be readily used in the field, the majority of their service life is spent with exposure to levels of moisture which can significantly impact upon their utility. As will be appreciated, moisture may be introduced into the detector from a number of sources, but is predominantly introduced through the primary inlet path of the inlet system, or by diffusion through an inlet membrane thereof, when not sampling. Moisture can also be intentionally introduced by, for example, means of a small flow of gas of a certain humidity.

HCE is a preferred negative mode dopant for use in a heated IMS detector. HCE is, however, unsuitable as a dopant in an unheated IMS detector, due to its high vapour pressure and the changes in HCE crystal structure which occur in response to changes in temperature. PCE has been found to overcome such problems and thus has emerged as a preferred negative mode dopant for use in unheated IMS detectors.

However, it has been found that a problem with using PCE as a dopant in a negative mode IMS detector is that it interacts with $O_2^-$ and free electrons in the reaction region, leading to the generation of two distinct reactant ion species, or and $Cl^-$ and $Cl^-.OOH$. These PCE related ion species may be detected as two distinct reactant ion peaks (RIPs) and observed in the IMS spectrum. Thus, when an analysed sample contains a target chemical which is capable of reacting with both PCE related $Cl^-$ and $Cl^-.OOH$ ions, two corresponding product ion peaks (PIPs) may also be detected and observed in the IMS spectrum.

Generally, the formation of two reactant ion species deriving from a dopant is less preferred than one reactant species, as the former can be associated with ion peak sensitivity issues which can negatively impact detection and identification of RIPs and PIPs. For instance, if only a single reactant ion is formed then the amplitude of the PIP formed following reaction of a target chemical with the single reactant ion is usually large, which facilitates detection and subsequent analysis. However, if, for example, the corona discharge of an IMS detector is shared in the formation of two reactant ion species deriving from the dopant, then the amplitudes the PIPs formed from reaction with both reactant ions are in most cases appreciably lower, which can make detection and subsequent analysis potentially more difficult. This is of course compounded where there are significant levels of "noise" in the IMS spectra as a result of interference compounds. Consequently, the risk of false positives/negatives may be increased.

Furthermore, moisture in the IMS cell also plays a key role in the resolution of the two RIPs associated with or and $Cl^-.OOH$ reactant ion species; the drier the IMS cell the better the resolution. The effect of moisture on resolution is a result of clustering, which is a well-known phenomenon whereby neutral molecules inside the IMS detector, such as water, air, carbon dioxide and volatile organic compounds, associate with ions traversing the drift chamber. Clustering around an ion affects its mobility. Thus, ions which are more susceptible to clustering may have reduced mobilities in the drift chamber, and thus longer drift times.

In a sufficiently dry IMS detector, the mobilities of the two PCE related ion species, $Cl^-$ and $Cl^-.OOH$, are sufficiently different so that they appear as two resolved RIPs upon detection. However, when moisture levels in the drift region are higher, and depending on the environmental conditions, it has been found that the two ion species are not completely resolved in the IMS spectrum. This is a result of differences in the clustering of the two PCE related reactant ions with water molecules, which affects their respective drift times to different extents. Typically, the $Cl^-$ ion clusters with water molecules to a far greater extent than the $Cl^-.OOH$ ion such that the mobility of the $Cl^-$ ion through the drift chamber is reduced to a level similar to that of the larger $Cl^-.OOH$ ion, leading in some cases to a single overlapped RIP in the IMS spectrum.

In order for PCE to be used effectively as a dopant, it is crucial to be able to measure and/or control the respective formation of the two PCE related $Cl^-$ and $Cl^-.OOH$ ion species in order to predict the IMS response to target chemicals which can react with one or both PCE related ion species and produce characteristic PIPs. This is particularly the case when an unheated IMS detector can be expected to spend up to 80% of its service life being operated under conditions where the levels of moisture are high enough to have a significant impact on the dominant chemistry inside the detector and the drift times through the drift chamber. The ability to predict the IMS response greatly assists in the identification of target chemicals. For instance, it is possible to adjust the window position (corresponding to a range of drift time over which ion peaks may be visualised) so as to visualise the PIPs across a range of drift time which is appropriate having regard to the expected drift time and amplitude of the target chemical's PIPs. This is of particular benefit in reducing false positives/negatives and improving confidence in the IMS spectral data.

Moreover, the ability to adjust the conditions under which the PCE doped IMS detector is operated in order to favour the formation of one of the two PCE related ion species over another would be particularly beneficial. This may allow one of the PCE related ion species to be formed almost exclusively over the other, such that the amplitude of the corresponding PIP which is formed may be larger, facilitating detection and subsequent analysis, and thereby overcoming the disadvantages of forming two dopant related reactant ions discussed hereinbefore. As will be appreciated, if a target chemical only reacts with one of the PCE related reactant ions, it is particularly advantageous to be able to measure the ratio of the ions and adjust, if necessary, the operating conditions of the IMS detector so as to favour production of that particular reactant ion over the other.

Alternatively, the conditions under which the PCE doped IMS detector is operated could be adjusted so as to produce a desired ratio of the two reactant ion species. This may allow two PIPs to be formed with a characteristic ratio of amplitudes, or at least individual amplitudes which are large enough for ease of detection and analysis, under a particular set of operating conditions for the PCE doped IMS detector. This may represent an alternative means for facilitating target chemical identification, by effectively providing two window positions which may be analysed.

This disclosure relates to the surprising finding that 1-chloro-2,2,2-trifluoroethyl difluoromethyl ether, also known as isoflurane (CAS number: 26675-46-7), as a means for determining the ratio of the PCE related ion species, $Cl^-$ and $Cl^-.OOH$, in a negative mode PCE doped IMS detector.

In a first aspect of the disclosure, there is provided a process for determining the ratio of $Cl^-$ to $Cl^-.OOH$ reactant ion species formed in a pentachloroethane doped ion mobility spectrometer operating in negative mode, said process comprising:

i) introducing a sample comprising or consisting essentially of isoflurane into a pentachloroethane doped ion mobility spectrometer;

ii) collecting data relevant to the detection of two isoflurane monomer ions formed following reaction with $Cl^-$ and $Cl^-.OOH$ reactant ion species present in the pentachloroethane doped ion mobility spectrometer; and iii) determining the ratio of $Cl^-$ to $Cl^-.OOH$ reactant ion species formed in the pentachloroethane doped ion mobility spectrometer based on an evaluation of the data collected.

Embodiments of the disclosure will now be described, by way of example only, with reference to the accompanying Figures, in which.

Figure 1:
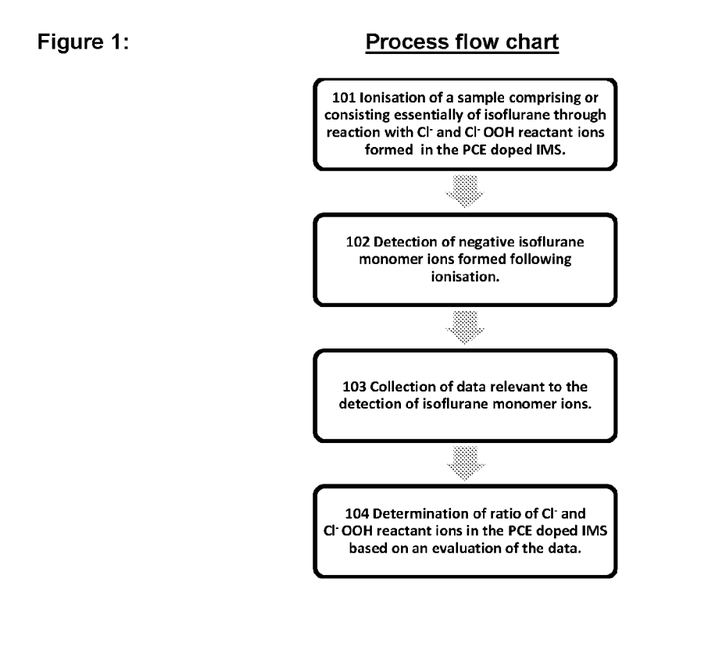
FIG. 1 corresponds to a flow chart illustrative of the process of the present disclosure.

In the example illustrated in FIG. 1, the first part of the process 101 involves ionisation of a sample comprising or consisting essentially of isoflurane with PCE related reactant ions or and $Cl^-.OOH$ formed in a PCE doped IMS detector. Isoflurane, whose chemical structure is depicted below, is known for its use as an anesthetic, frequently used in veterinary anaesthesia, and typically exists in the form of a racemic mixture of (R) and (S) optical isomers.

A particular advantage of isoflurane is that it reacts with both of the PCE related reactant ions C⁻ and Cl⁻.OOH without significant preference to produce distinct isoflurane monomer ions. Thus, the sample comprising or consisting essentially of isoflurane is introduced into a PCE doped IMS detector where it is ionised in the reaction region upon interaction with PCE related C⁻ and Cl⁻.OOH reactant ion species present therein. Upon ionisation, isoflurane forms negative monomer ions. Reference herein to negative isoflurane monomer ions corresponds to [CF₃CH(Cl)OCF₂H—Cl]⁻ and [CF₃CH(Cl)OCF₂H—Cl.OOH]⁻ adducts. The proportions of the two negative monomer ions formed is dependent on the dominant reactant ion chemistry within the detector, which can be modified, for instance, by adjusting operating conditions of the PCE doped IMS detector.

In the process example illustrated in FIG. 1, there is detection 102 of the negative isoflurane monomer ions formed as a result of ionisation by the detector. The ion mobility spectrometer operating in negative mode typically comprises: a drift chamber between an ioniser and detector along which ions can travel from the ioniser toward the detector; a gate for controlling the passage of ions from the ioniser to the drift chamber; and a plurality of electrodes configured to provide a negative uniform electric field gradient within the drift chamber for transporting ions from the ioniser toward the detector. The detector may be linked to an analysis unit. In some embodiments, the analysis unit comprises a computer system. Said computer system may comprise computer program products, and may be recorded on non-transitory computer readable media, and these may be operable to program a processor to perform any one or more of the processes described herein.

The process illustrated in FIG. 1 comprises collection of data 103 relevant to the detection of the negative isoflurane monomers formed as a result of ionisation with PCE related Cl⁻ and Cl⁻.OOH reactant ions. The data obtained as part of the process of the present disclosure may comprise amplitudes and preferably also drift times through the drift chamber for the negative isoflurane monomer ions formed following ionisation. Where the detector of the ion mobility spectrometer is linked to an analysis unit, the analysis unit may be configured to collect data relevant to the detection of isoflurane monomer ions formed as a result of ionisation with PCE related Cl⁻ and Cl⁻.OOH reactant ions.

The process example illustrated in FIG. 1 comprises determination 104 of the ratio of or and Cl⁻.OOH reactant ions in the IMS. In other words, the dominant chemistry governing the production of PCE related Cl⁻ and Cl⁻.OOH reactant ions can be assessed. In some embodiments, this part of the process may comprise evaluating the amplitude ratio of the two isoflurane monomer ion peaks; the amplitudes of the two isoflurane monomer ion peaks being a function of the amount of Cl⁻ and Cl⁻.OOH reactant ions present for ionisation. Where a ratio of isoflurane monomer product ions has been determined using the PCE doped ion mobility detector, the determined ratio may subsequently be verified through separate mass spectrometer (MS) analysis.

In another aspect, the present disclosure relates to a system for determining the ratio of Cl⁻ to Cl⁻.OOH reactant ion species formed in a pentachloroethane doped ion mobility spectrometer operating in the negative mode, said system comprising: a pentachloroethane doped ion mobility spectrometer; a sample comprising or consisting of isoflurane; and an analysis unit configured to:
  i) collect data relevant to the detection of two isoflurane monomer ions formed following ionisation with Cl⁻ and Cl⁻.OOH reactant ion species present in the pentachloroethane doped ion mobility spectrometer following introduction of the isoflurane sample; and
  ii) determine the ratio of Cl⁻ to Cl⁻.OOH reactant ion species formed in the pentachloroethane doped ion mobility spectrometer based on an evaluation of the data collected.

Figure 2:
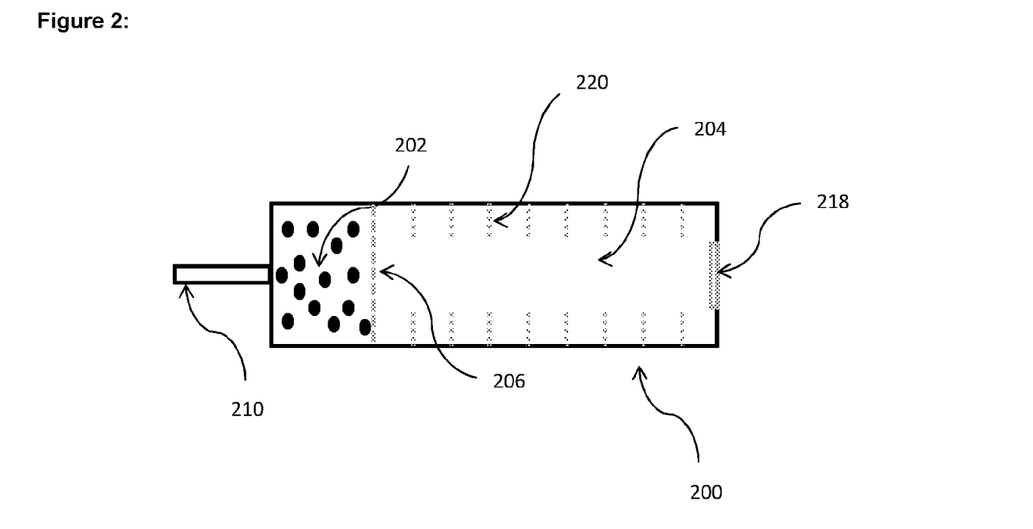
FIG. 2 shows an ion mobility spectrometer of use accordance with the present disclosure.

FIG. 2 is an illustration of an ion mobility spectrometer 200 which includes an ionisation chamber 202 that is separated from a drift chamber 204 by a gate 206. The gate 206 can control passage of ions from the ionisation chamber 202 into the drift chamber 204. In FIG. 2, an ionisation source 210 is arranged for ionising material in the ionisation chamber 202. In the example illustrated in FIG. 2, the drift chamber 204 lies between the ionisation chamber 202 and a detector 218, so that ions can reach the detector 218 by traversing the drift chamber 204. The drift chamber 204 may comprise a series of electrodes 220 for applying an electric field in the drift chamber to move ions from the ionisation chamber 202 along the drift chamber 204 toward the detector 218. The ion mobility spectrometer 200 may be configured to provide a flow of carrier gas in a direction generally opposite an ion's path of travel to the detector 218. For example, the carrier gas can flow from adjacent the detector 218 toward the gate 206.

The detector 218 may be used to characterise the ions detected based on the time for ions to pass from the gate 206 along the drift chamber 204 to the detector 218. Examples of a detector 218 are configured to provide a signal indicating that ions have arrived at the detector 218. For example, the detector may comprise a faraday plate, which generates an electrical current when ions are neutralised against it.

Electrodes 220 may be arranged to guide ions toward the detector 218, for example the electrodes 220 may comprise rings which may be arranged around the drift chamber 204 to focus ions onto the detector 218. Although the example of FIG. 2 includes a plurality of electrodes 220, in some examples only two electrodes may be used, or a single electrode may be used in combination with the detector 218 to apply an electric field to guide ions toward the detector 218. Other electrode configurations are also possible, examples include, but are not limited to electrodes of other geometric shapes and electrically resistive and/or conductive (e.g., a resistive electrical conductor) coatings, such as a continuous coating.

Although not shown in FIG. 1, the process of the present disclosure may further comprise adjusting at least one detection parameter of the pentachloroethane doped ion mobility spectrometer based on the determined ratio of Cl⁻ to Cl⁻.OOH reactant ion species, in order to facilitate detection of a target chemical in a sample to be analysed using the pentachloroethane doped ion mobility spectrometer. The target chemical may, for instance, be an explosive, such as cyclotrimethylenetrinitramine (RDX), nitroglycerine (NG), or 2,4,6-trinitrotoluene (TNT), a chemical warfare agent or an industrial chemical.

In some embodiments, the at least one detection parameter to be adjusted is the product ion drift time detection parameter of the pentachloroethane doped ion mobility spectrometer. Thus, the detection window position may be adjusted (i.e. the range of drift time over which ion peaks may be visualised) so as to improve visualisation of PIP(s) formed from reaction of PCE related $Cl^-$ and $Cl^-.OOH$ reactant ions. For instance, if it is determined from the ratio of $Cl^-$ to $Cl^-.OOH$ reactant ion species that one ion is present in major proportion under the particular operating conditions of the IMS detector, the window position may be adjusted accordingly for the detection of the PIP which is formed from reaction with that major ion. Alternatively, two window positions could be fixed for the detection of two PIPs formed through reaction with both of the PCE related reactant ions if, for example, there is a similar proportion of $Cl^-$ vs $Cl^-.OOH$ reactant ion species being formed. In both cases, the identification of target chemicals from the spectral data is assisted. Where an analysis unit is implemented as a means for carrying out these embodiments of the process, the analysis unit may be configured to determine the ratio of $Cl^-$ to $Cl^-.OOH$ reactant ion species and adjust at least one detection parameter of the IMS detector, such as a product ion drift time detection parameter (i.e. detection window position).

Although not shown in FIG. 1, the example process may further comprise adjusting at least one operating condition of the ion mobility spectrometer so as to favour formation of one of $Cl^-$ or $Cl^-.OOH$ reactant ion species in the pentachloroethane doped ion mobility spectrometer based on the determined ratio of $Cl^-$ to $Cl^-.OOH$ reactant ion species. The at least one operating condition to be adjusted may, for instance, be selected from a) concentration of PCE dopant in the reaction region of the ion mobility spectrometer, b) total carrier gas volume; c) carrier gas flow rate; d) location and/or direction of injection of PCE dopant into the ion mobility spectrometer; or e) the level of humidity in the ion mobility spectrometer, or combinations thereof. As will be appreciated by the skilled person, it is possible to inject a small flow of gas of a certain humidity into the ion mobility spectrometer to thereby adjust the overall humidity under which the ion mobility spectrometer operates. However, since increasing humidity may negatively impact upon resolution, it is preferred that the operating conditions to be adjusted are selected from a) to d) described above.

Being able to control the formation of the PCE related reactant ions by adjusting operating conditions of the IMS detector is particularly advantageous since it allows the dominant chemistry of the IMS detector to be tailored in view of the prevailing environmental conditions, as well as based on the nature of the target chemical in the sample to be analysed. As will be appreciated, if a target chemical only reacts with one of the PCE related reactant ions, it is particularly advantageous to be able to adjust the operating conditions of the IMS detector so as to favour production of that particular reactant ion over the other.

Figure 3:
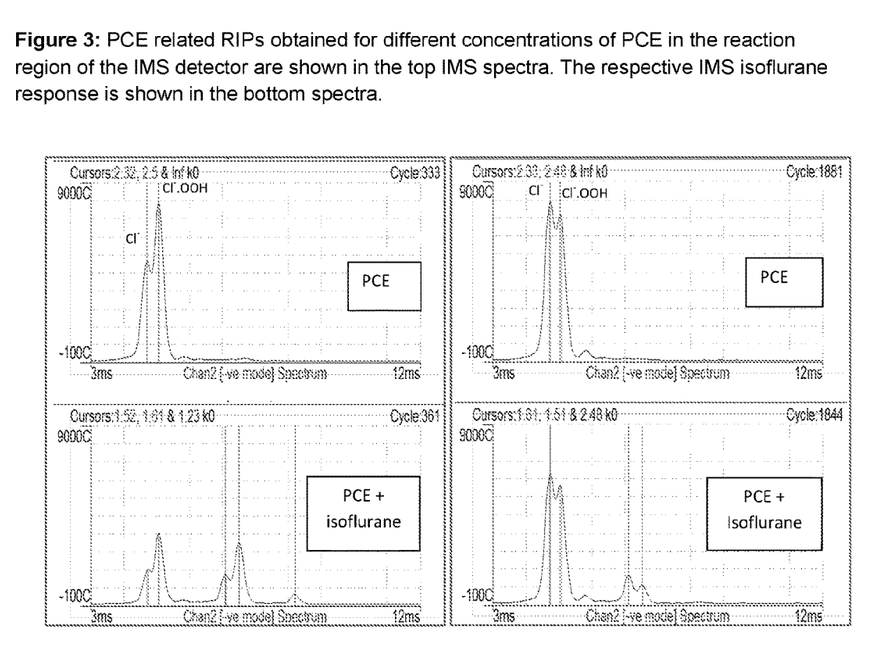
FIG. 3 corresponds to a series of IMS spectra showing amplitude and drift times of PCE related RIPs at different PCE concentrations, as well as the respective IMS response when isoflurane is introduced into the PCE doped ion mobility spectrometer at the different PCE concentrations.

Concentration of the PCE dopant in the reaction region of the IMS detector has an effect on the dominant chemistry within the IMS detector. In particular, at least in some instances, the concentration of the PCE dopant dictates whether the formation of the $Cl^-$ or $Cl^-.OOH$ reactant ion species is favoured over the other. The PCE concentration affects the amplitude ratio of the PCE related $C^-$ and $Cl^-.OOH$ RIPs. This is illustrated in FIG. 3. Changes in PCE dopant concentration affects the relative proportions of PCE related $Cl^-$ and $Cl^-.OOH$ ion species formed. This can clearly be seen when comparing the two top IMS spectra of FIG. 3. Similarly, the respective isoflurane response in the bottom spectra of FIG. 3, also shows a corresponding change in the amplitude ratio of the isoflurane monomer ion peaks.

Thus, the concentration of PCE dopant, to the extent that it is able to modify the dominant chemistry within the detector, affects the amplitude ratio of the PCE related RIPs observed in the IMS spectrum. As illustrated in FIG. 3, this may also be reflected in the respective IMS response of isoflurane, where other operating conditions, such as moisture level; carrier gas volume and flow rate; and direction of PCE injection remain constant.

It will also be appreciated by the person of skill in the art that adjusting the total carrier gas volume; carrier gas flow rate; or the location and/or direction of injection of PCE dopant into the ion mobility spectrometer are known ways of manipulating the distribution of dopant within the reaction region of the ion mobility spectrometer. Thus, certain optimal areas of the ion mobility spectrometer can be targeted by adjusting any of these operating conditions so as to modify the nature of the reactions in the ionisation region. Thus, the dominant chemistry within the ion mobility spectrometer can be readily modified by adjusting the operating conditions. As such, the skilled person is able to adjust operating conditions so as to favour the formation of one of the two PCE related reactant ions over the other, as desired.

It has been surprisingly found that the resolution of the isoflurane monomer ion peaks is unaffected by the level of moisture in the IMS detector. Unlike $Cl^-$ and $Cl^-.OOH$ reactant ions which cluster differently with water molecules present in the drift region of the ion mobility spectrometer, the corresponding isoflurane monomer ions, $[CF_3CH(Cl)OCF_2H-Cl]^-$ and $[CF_3CH(Cl)OCF_2H-Cl.OOH]^-$, cluster to similar extents. Thus, the more mobile $[CF_3CH(Cl)OCF_2H-Cl]^-$ ion has a shorter drift time than the less mobile $[CF_3CH(Cl)OCF_2H-Cl.OOH]^-$, regardless of the level of moisture and the extent of clustering in the drift region of the ion mobility spectrometer.

Figure 4:
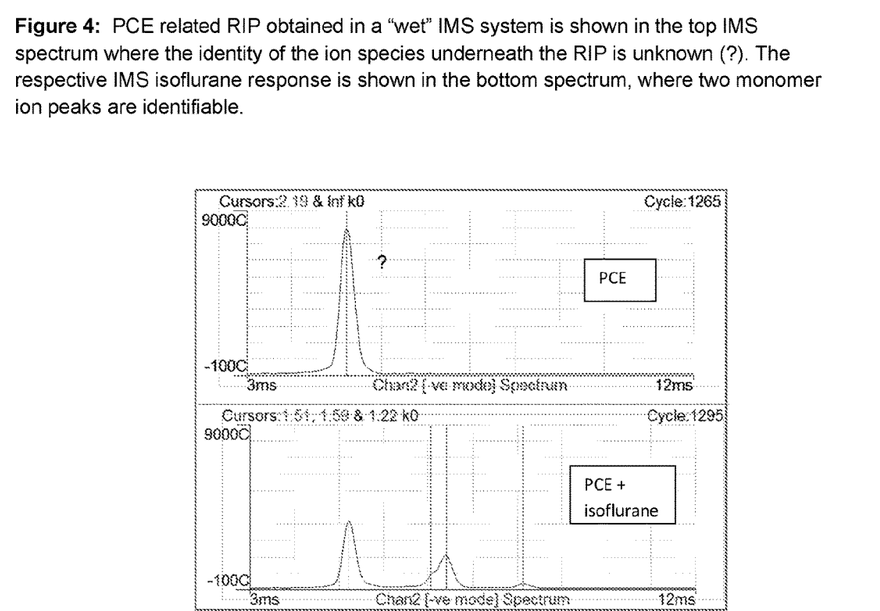
FIG. 4 shows an IMS spectrum comprising a single RIP obtained for a PCE doped ion mobility spectrometer operated under "wet" conditions (e.g. with a moisture level over 10 ppm in the carrier gas). The IMS response for isoflurane obtained with the same PCE doped ion mobility spectrometer operated under "wet" conditions is also provided, wherein it is clear that two isoflurane monomer ion peaks are identifiable, despite only one RIP being observed.

This is illustrated in FIG. 4. In a "wet" IMS system (e.g. where the amount of water vapour in the carrier gas is 10 ppm or more) the RIPs for $Cl^-$ and $Cl^-.OOH$ reactant ions are completely unresolved and appear only as a single RIP. Accordingly, it is impossible to accurately determine the ratio of the ion species underneath the RIP. In contrast, distinct isoflurane monomer peaks are identifiable in the IMS response of isoflurane, such that the amplitude ratio of the monomer ion peaks can still be determined. It is thus particularly advantageous to use isoflurane for determining the ratio of $Cl^-$ and $Cl^-.OOH$ reactant ions in a PCE doped IMS when the reactant ion peaks corresponding to $Cl^-$ and $Cl^-.OOH$ ion species are completely unresolved in the spectral data, as illustrated in FIG. 4. This is of course also the case when the two PCE related RIPs are separately identifiable, but there is overlap of the peaks such that they are at least partially unresolved. Where reference is made herein to peaks being at least partially unresolved, this is intended to mean where there is overlap of a plurality of peaks in the IMS spectrum, where overlap is at least to the extent that the area under overlapped peaks cannot be completely assigned to the detection of one ion over another.

Thus, the amplitude ratio of isoflurane monomer ion peaks can be used to accurately determine the ratio of $Cl^-$ and $Cl^-.OOH$ reactant ions in the reaction region of the ion mobility spectrometer, since the amplitudes of the monomers are a function of the amount of $Cl^-$ and $Cl^-.OOH$ reactant ions present. An understanding of the proportions of $Cl^-$ and $Cl^-.OOH$ reactant ions (i.e. the ratio of the of $Cl^-$ and $Cl^-.OOH$ reactant ions) formed in the reactant region of the ion mobility spectrometer affords an appreciation of the dominant chemistry and allows for a better prediction of the IMS response of a target chemical which is able to react with both Cl⁻ and Cl−.OOH reactant ions, under the particular operating conditions of the ion mobility spectrometer. This greatly assists identification of target chemicals.

For instance, once the ratio of Cl⁻ and Cl⁻.OOH reactant ions is determined at the particular operating conditions (including temperature and pressure) of the IMS detector, a prediction can be made as to the drift time of a particular target chemical product ion. This may, for instance, be first based on a selection of the particular product ion, for which detection may subsequently be optimised. For example, if it is determined that one PCE related reactant ion is present in higher proportion; the corresponding product ion formed through reaction with that ion may preferably be selected for detection. After this step, window positioning may be adjusted for visualising a suitable range of drift time, based on previously calculated drift times for that specific target chemical product ion under those operating conditions, or based on known reduced mobility values of the target chemical's product ion. Optionally, the selection of a suitable window may be adjusted following a step of calibration of the IMS detector with, for instance, an internal instrument standard.

Additionally, the ability to determine accurately the ratio of Cl⁻ and Cl⁻.OOH reactant ions allows for the operating conditions to be adjusted so as to change the proportion of Cl⁻ and Cl⁻.OOH reactant ions, as desired. This can be advantageous where visualisation of PIPs can be improved against noise in the IMS spectra by changing the proportions of Cl⁻ and Cl⁻.OOH reactant ions by adjusting operating conditions and thereby changing the amplitude ratio of PIPs observed. Moreover, by adjusting the operating conditions and being aware of consequential changes in the dominant reactant ion chemistry in the reaction region of the ion mobility spectrometer, multiple rounds of analysis can be used and consequential changes in the amplitude ratio of PIPs can be assessed in order to more reliably identify the presence a target chemical. This can further reduce the likelihood of false positives/negatives.

As will be appreciated by the skilled person, where reference is made herein to the ratio of Cl⁻ to Cl⁻.OOH reactant ion species, the ratio is an ion number ratio.

The process of present disclosure is suitable for use with unheated and heated ion mobility spectrometers. However, the process of the present disclosure is particularly suitable for use with an unheated ion mobility spectrometer, which operates at ambient temperature. In view of the application of ion mobility spectrometers, often ambient temperature can be extremely wide ranging such as from −31° C. to 50° C., including from −10° C. to 40° C. This range of temperature can have a significant effect on the peak positioning (drift time) of PIPs of target chemicals. By fixing temperature, as in a heated ion mobility spectrometer, changes in peak positioning as a result of changing temperature are substantially reduced. Nevertheless, isoflurane is also particularly advantageous in that it has a volatility which makes it suitable for use with an ion mobility spectrometer operating over a wide range of temperature.

The PCE doped ion mobility spectrometer described herein may comprise a drying agent, such as a molecular sieve, for drying carrier gas in the drift chamber. Moreover, as will be appreciated by the person of skill in the art, scrubbers may be employed to minimise contamination by volatile organic material. These components may reduce contamination in the drift chamber and/or the level of clustering of neutral molecules about ions in the drift chamber.

It will be appreciated that the ionisation source of the PCE doped ion mobility spectrometer may be selected from any suitable source for the purposes of ionisation. For instance, radioactive sources may be used, such as a $^{63}$Ni foil, electrospray ionisation, corona-spray and corona-discharge ionisation, matrix assisted laser desorption ionisation, or photoionisation sources.

The detector in the PCE doped ion mobility spectrometer of the present disclosure may simply be a plate that works as a Faraday cup. However, it will be appreciated that other detectors may be used in accordance with the present disclosure as an alternative or in addition thereto, for example a mass spectrometer.

The PCE doped ion mobility spectrometer may include a vapour generator to supply the PCE dopant and/or isoflurane sample to the ion mobility spectrometer, although any suitable means of which the skilled person is aware may be used. In some applications it is important that the vapour generator can be switched on and off rapidly, and that leakage can be prevented when the ion mobility spectrometer is switched off. For example, rapid switching of the vapour generator on and off enables rapid switching between different doping conditions, such as different levels of dopant. Such rapid switching could also enable different regions of the ion mobility spectrometer are doped differently by ensuring there was no leakage to undoped regions of the apparatus when the apparatus is switched off.

In embodiments of the present disclosure, the dopant and/or the isoflurane sample may be introduced into the detection apparatus by means of an on-demand vapour generator comprising: a vapour source comprising the calibrant sample coupled by a flow path to provide vapour through an impeder to an outlet for dispensing vapour to the detection apparatus. The impeder may comprise: a first vapour permeable passage arranged to impede diffusion of the vapour from the source to the outlet. The first vapour permeable passage may comprise a material adapted to take up the vapour, such as by absorption. Absorption comprises at least one of adsorbing the vapour onto a surface, chemical absorption, take up of the vapour by chemical or molecular action, and at least temporary capture of the vapour in a porous material. The vapour permeable passage is configured to enable vapour to be driven through a diffusion barrier from the source to the outlet by a pressure difference (e.g. pumped or forced flow as opposed to simply a difference in concentration).

The vapour generator may also comprise at least one additional vapour permeable passage to act as a sink, coupled to the outlet by the first vapour permeable passage. The sink can comprise a material adapted to take up the vapour to divert diffusion of vapour away from the outlet. In some embodiments, the first vapour permeable passage and the sink are arranged so that, in response to a pressure difference between the outlet and the vapour source, resistance to driving vapour flow through the first vapour permeable passage to the outlet is less than the resistance to driving vapour flow into the sink. In some embodiments, the flow path comprises a branch that couples the vapour source to the first vapour permeable passage, and an enclosed branch comprising the sink. In some embodiments, the sink comprises at least one second vapour permeable passage, the vapour source comprises a vapour chamber, and the impeder comprises an absorption assembly. Suitable on-demand vapour generators which are preferably used in connection with the present disclosure are described in WO 2014/045067.

In a further aspect, the present disclosure also relates to use of isoflurane for optimising at least one detection parameter of a pentachloroethane doped ion mobility spectrometer operating in the negative mode for the identification of a target chemical. Preferably, the detection parameter to be optimised is a drift time detection parameter (i.e. window position). Such a use involves determining the ratio of Cl⁻ to Cl⁻.OOH reactant ions formed in a pentachloroethane doped ion mobility spectrometer so as to predict the IMS response of a target chemical, as described hereinbefore. Thus, a sample comprising or consisting of isoflurane may be introduced into the pentachloroethane doped ion mobility spectrometer and data relevant to the detection of two isoflurane monomer ions formed following reaction with Cl⁻ and Cl⁻.OOH reactant ion species may be obtained and evaluated. Preferably, the data comprises the ratio of peak amplitudes for the two isoflurane monomer ion peaks in spectral data obtained from the pentachloroethane doped ion mobility spectrometer.

Embodiments of the present disclosure described hereinbefore may be combined with any other compatible embodiments to form further embodiments of the disclosure.

The invention claimed is:

1. A process for determining the ratio of Cl—to Cl—.OOH reactant ion species formed in a pentachloroethane doped ion mobility spectrometer operating in the negative mode, the process comprising:
   introducing a sample comprising isoflurane into a pentachloroethane doped ion mobility spectrometer;
   collecting data relevant to the detection of two isoflurane monomer ions, the two isoflurane monomer ions being formed following reaction of the sample with Cl— and Cl—.OOH reactant ion species present in the pentachloroethane doped ion mobility spectrometer; and
   determining the ratio of Cl— to Cl—.OOH reactant ion species formed in the pentachloroethane doped ion mobility spectrometer based on an evaluation of the data collected.

2. The process according to claim 1, wherein the data which is collected comprises the ratio of peak amplitudes for the two isoflurane monomer ion peaks in spectral data obtained from the pentachloroethane doped ion mobility spectrometer.

3. The process according to claim 1, wherein reactant ion peaks corresponding to Cl— and Cl—.OOH ion species are at least partially unresolved in the spectral data obtained from the pentachloroethane doped ion mobility spectrometer.

4. The process according to claim 3, wherein the amount of water vapour in the carrier gas is 10 ppm or above.

5. The process according to claim 1, further comprising adjusting at least one detection parameter of the pentachloroethane doped ion mobility spectrometer based on the determined ratio of Cl— to Cl—.OOH reactant ion species in order to facilitate detection of a target chemical in a sample to be analysed using the pentachloroethane doped ion mobility spectrometer.

6. The process according to claim 5, wherein the target chemical comprises at least one of an explosive a chemical warfare agent, or an industrial chemical.

7. The process according to claim 6, wherein the target chemical is an explosive selected from the group consisting of cyclotrimethylenetrinitramine (RDX), nitroglycerine (NG), and 2,4,6-trinitrotoluene (TNT).

8. The process according to claim 5, wherein the at least one detection parameter to be adjusted is the product ion drift time detection parameter of the pentachloroethane doped ion mobility spectrometer.

9. The process according to claim 1, further comprising adjusting at least one operating condition of the ion mobility spectrometer so as to favour formation of one of the Cl— or Cl—.OOH reactant ion species in the pentachloroethane doped ion mobility spectrometer based on the determined ratio of the Cl— to Cl—.OOH reactant ion species.

10. The process according to claim 9, wherein the at least one operating condition to be adjusted comprises at least one of a concentration of PCE dopant in the reaction region of the ion mobility spectrometer, total carrier gas volume; carrier gas flow rate; location and/or direction of injection of PCE dopant into the ion mobility spectrometer; direction of injection of PCE dopant into the ion mobility spectrometer; or the level of humidity in the ion mobility spectrometer.

11. The process according to claim 1, wherein the sample consists essentially of isoflurane.

12. The process according to claim 1, wherein the sample is introduced to the ion mobility spectrometer by an on-demand vapour generator.

13. A system for determining the ratio of Cl— to Cl—.OOH reactant ion species formed in a pentachloroethane doped ion mobility spectrometer operating in the negative mode, said system comprising:
   a pentachloroethane doped ion mobility spectrometer;
   a sample comprising isoflurane; and
   an analysis unit configured to:
      collect data relevant to the detection of two isoflurane monomer ions, the two isoflurane monomer ions being formed following ionisation with Cl— and Cl—.OOH reactant ion species present in the pentachloroethane doped ion mobility spectrometer following introduction of the sample; and
      determine the ratio of Cl— to Cl—.OOH reactant ion species formed in the pentachloroethane doped ion mobility spectrometer based on an evaluation of the data collected.

14. The system according to claim 13, further comprising an on-demand vapour generator for introducing at least one of a dopant or the sample into the ion mobility spectrometer.

15. The system according to claim 13, wherein the analysis unit comprises a computer system.

16. The system according to claim 13, wherein the sample consists essentially of isoflurane.

17. A method of optimising at least one detection parameter of a pentachloroethane doped ion mobility spectrometer for the identification of a target chemical, comprising:
   introducing a sample comprising isoflurane into a pentachloroethane doped ion mobility spectrometer operating in the negative mode;
   collecting data relevant to the detection of two isoflurane monomer ions, the two isoflurane monomer ions being formed following reaction of the sample comprising isoflurane with Cl— and Cl—.OOH reactant ion species present in the pentachloroethane doped ion mobility spectrometer;
   adjusting at least one detection parameter of the pentachloroethane doped ion mobility spectrometer based on the data collected in order to facilitate detection of a target chemical in a sample to be analysed using the pentachloroethane doped ion mobility spectrometer.

18. The method according to claim 17, further comprising determining the ratio of Cl— to Cl—.OOH reactant ion species formed in the pentachloroethane doped ion mobility spectrometer based on an evaluation of the data collected.

19. The method according to claim 18, wherein the at least one detection parameter is adjusted based on the ratio of Cl— to Cl—.OOH reactant ion species.

\* \* \* \* \*